(12) United States Patent
Suzuki et al.

(10) Patent No.: US 8,703,247 B2
(45) Date of Patent: Apr. 22, 2014

(54) CROSS SECTION PROCESSING METHOD AND METHOD OF MANUFACTURING CROSS SECTION OBSERVATION SAMPLE

(75) Inventors: Hidekazu Suzuki, Chiba (JP); Toshiaki Fujii, Chiba (JP); Mike Hassel-Shearer, Northridge, CA (US)

(73) Assignees: SII Nanotechnology Inc., Chiba (JP); SII Nanotechnology USA Inc., Northridge, CA (US)

( * ) Notice: Subject to any disclaimer, the term of this patent is extended or adjusted under 35 U.S.C. 154(b) by 497 days.

(21) Appl. No.: 12/693,580

(22) Filed: Jan. 26, 2010

(65) Prior Publication Data

US 2010/0189917 A1    Jul. 29, 2010

(30) Foreign Application Priority Data

Jan. 27, 2009    (JP) .................... 2009-014925

(51) Int. Cl.
| | | |
|---|---|---|
| C23C 14/00 | (2006.01) | |
| C23C 14/02 | (2006.01) | |
| C23C 14/04 | (2006.01) | |
| C23C 14/12 | (2006.01) | |
| C23C 14/14 | (2006.01) | |
| C23C 14/20 | (2006.01) | |
| H05H 1/00 | (2006.01) | |

(52) U.S. Cl.
USPC ........... 427/523; 427/525; 427/526; 427/531; 427/533; 427/534

(58) Field of Classification Search
USPC ............. 427/523, 525, 526, 531, 533, 534; 216/66, 87, 94; 204/192.11, 192.34; 250/492.21
See application file for complete search history.

(56) References Cited

U.S. PATENT DOCUMENTS

| | | | |
|---|---|---|---|
| 5,028,780 A * | 7/1991 | Kaito et al. | 250/307 |
| 6,639,226 B2 * | 10/2003 | Morio et al. | 250/491.1 |
| 8,080,935 B2 * | 12/2011 | Yoshida et al. | 313/504 |
| 2004/0110367 A1 * | 6/2004 | Kumakura et al. | 438/613 |
| 2004/0261719 A1 | 12/2004 | Arjavac et al. | |
| 2006/0157341 A1 * | 7/2006 | Fujii | 204/192.34 |
| 2007/0158590 A1 | 7/2007 | Hagiwara et al. | |
| 2008/0073586 A1 | 3/2008 | Iwasaki | |
| 2008/0142735 A1 | 6/2008 | Chandler et al. | |
| 2010/0008563 A1 * | 1/2010 | Fujii et al. | 382/149 |

FOREIGN PATENT DOCUMENTS

| | | |
|---|---|---|
| JP | 02-152155 A | 6/1990 |
| JP | 2005-015922 A | 1/2005 |
| JP | 2005-317330 A | 11/2005 |
| JP | 2007-103108 A | 4/2007 |
| JP | 2007-193977 A | 8/2007 |
| JP | 2007-220344 A | 8/2007 |
| JP | 2008-177154 A | 7/2008 |
| JP | 2009-004126 A | 1/2009 |

* cited by examiner

*Primary Examiner* — Dah-Wei D Yuan
*Assistant Examiner* — Diane Zhang
(74) *Attorney, Agent, or Firm* — Brinks Gilson & Lione

(57) ABSTRACT

A cross section processing method to be performed on a sample by irradiating the sample having a layer or a structure of an organic substance on a surface at a cross section processing position thereof with a focused ion beam using a focused ion beam apparatus includes: a protective film forming step for forming a protective film on the surface of the layer or the structure of the organic substance by irradiating the surface of the sample including the cross section processing position with the focused ion beam under the existence of source gas as the protective film; and a cross section processing step for performing cross section processing by irradiating the cross section processing position formed with the protective film with the focused ion beam at a voltage higher than an accelerating voltage in the protective film forming step.

11 Claims, 9 Drawing Sheets

FIG. 4(a)     FIG. 4(b)     FIG. 4(c)
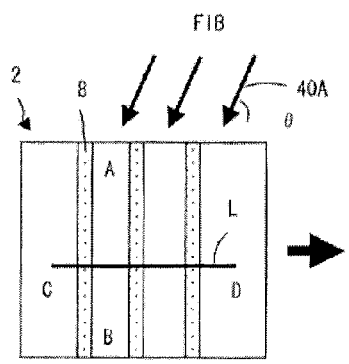 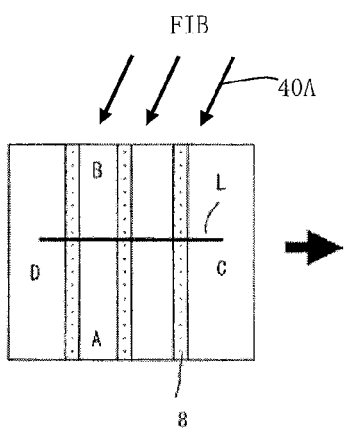 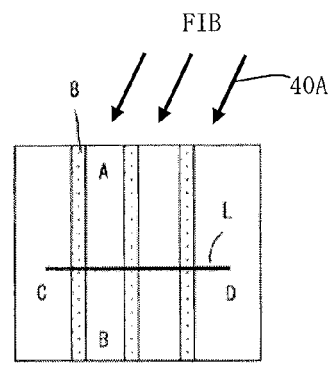
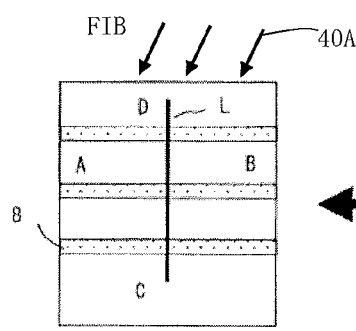 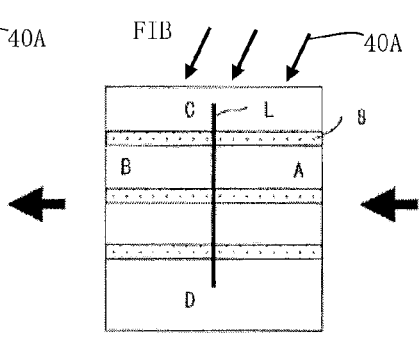
FIG. 4(f)     FIG. 4(e)     FIG. 4(d)

FIG. 6(g)
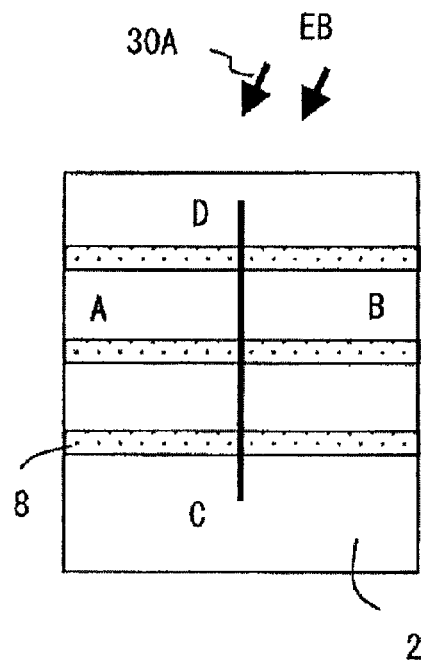
FIG. 6(h)
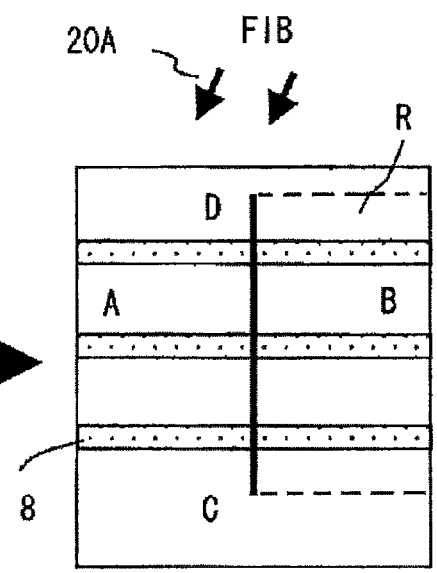
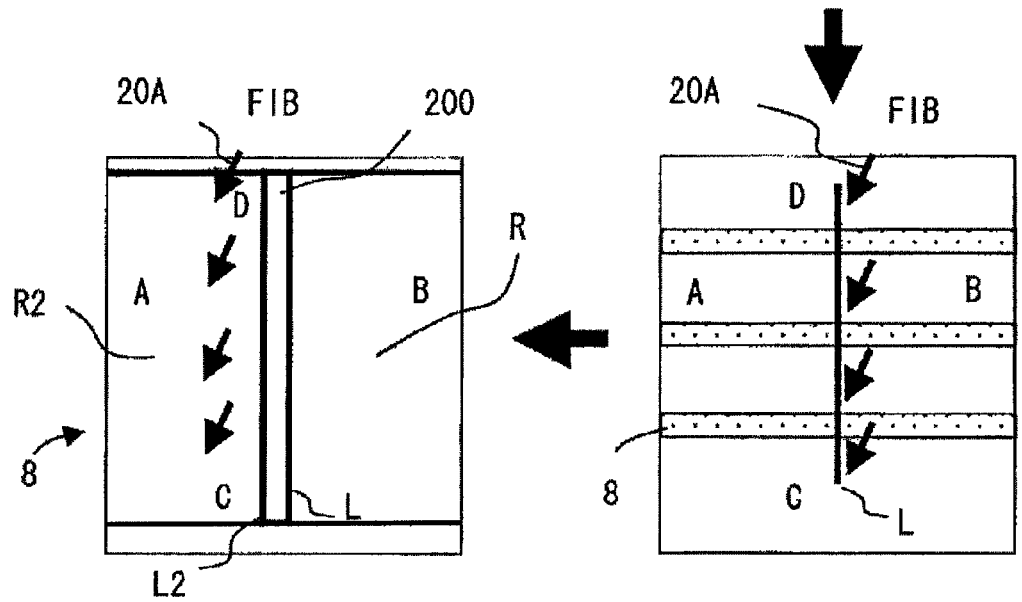
FIG. 6(j)  FIG. 6(i)

CROSS SECTION PROCESSING METHOD AND METHOD OF MANUFACTURING CROSS SECTION OBSERVATION SAMPLE

RELATED APPLICATIONS

This application claims priority under 35 U.S.C. §119 to Japanese Patent Application No. 2009-014925 filed on Jan. 27, 2009, the entire content of which is hereby incorporated by reference.

BACKGROUND OF THE INVENTION

1. Technical Field of the Invention

The present invention relates to a method of processing cross sections of samples using a focused ion beam for, for example, observing cross sections of a semiconductor devices or manufacturing samples for TEM (transmission electron microscope), and a method of manufacturing cross section observation samples.

2. Description of the Related Art

Samples having micropatterns such as semiconductor devices or semiconductor laser devices are increasingly miniaturized. Therefore, cross section processing is generally performed with FIB (focused ion beam) when observing the cross sections of the samples with an SEM (scanning electron microscope) or when slicing these samples into thin sections for fabricating samples for TEM (transmission electron microscope).

When the cross section processing is performed on a sample having projections and depressions on a surface thereof, there is a problem such that the etching speed by the FIB is fluctuated because of the influence of the projections and depressions, so that vertical lines are formed on a cross-sectional surface. Therefore, as a technique to form a film on the surface of the sample by CVD (chemical vapor deposition) induced by the FIB before performing the cross section processing is known (JP-A-2-152155).

In contrast, in recent years, in the semiconductor processing for example, there is a demand for performing the cross section processing of the samples having a resist pattern on the surfaces thereof or the fabrication of the TEM sample with the FIB in order to confirm whether the resist patterns are formed with high degree of accuracy.

However, when an attempt is made to perform a processing of the cross section of the sample on which an organic substance such as a resist film or the like on the surface thereof with the FIB, there arises a problem such that the fragile organic substance becomes damaged by the FIB, and hence the shape or the structure is changed (deformed), so that sufficient observation of the cross section cannot be achieved. Even when a protective film is formed by the FIB induced CVD before the cross section processing as described in JP-A-2-152155, the organic substance becomes damaged by the FIB emitted in this procedure. In contrast, even when the protective film is formed on the sample before the cross section processing by an electron beam, the organic substance on the sample is deformed.

SUMMARY OF THE INVENTION

In order to solve the problem described above, it is an object of the invention to provide a cross section processing method and a method of manufacturing cross section observation samples which achieve acquisition of cross section of samples having an organic substance formed on a surface thereof with high degree of accuracy.

In order to achieve the object as described above, a cross section processing method according to the invention is a cross section processing method to be performed on a sample by irradiating the sample having a layer or a structure of an organic substance on a surface at a cross section processing position thereof with a focused ion beam using a focused ion beam apparatus including: a protective film forming step for forming a protective film on the surface of the layer or the structure of the organic substance by irradiating the surface of the sample including the cross section processing position with the focused ion beam under the existence of source gas as the protective film; and a cross section processing step for performing cross section processing by irradiating the cross section processing position formed with the protective film with the focused ion beam at a voltage higher than an accelerating voltage in the protective film forming step.

In this configuration, damage caused by the ion beam on the organic substance on the surface of the sample is reduced when forming the protective film, so that a cross section of the sample with high degree of accuracy is acquired while preventing the organic substance from becoming damaged.

Also, a cross section processing method according to the invention is a cross section processing method to be performed on a sample by irradiating the sample having a layer or a structure of an organic substance on a surface at a cross section processing position thereof with a focused ion beam using a focused ion beam apparatus including: a protective film forming step for irradiating the surface of the sample including the cross section processing position with the focused ion beam at a first accelerating voltage and then irradiating the surface of the sample with the focused ion beam at a second accelerating voltage which is higher than the first accelerating voltage under the existence of source gas as a protective film; and a cross section processing step for performing cross section processing by irradiating the cross section processing position formed with the protective film with the focused ion beam at a third accelerating voltage which is higher than the first accelerating voltage.

In this configuration, damage by the ion beam when forming the protective film firstly on the organic substance on the surface of the sample is reduced, so that a cross section of the sample with high degree of accuracy is acquired while preventing the organic substance from becoming damaged. After having formed the protective film firstly, the protective film can be formed efficiently with a high accelerating voltage.

Preferably, the sample includes an alignment portion whose positional relationship with the cross section processing position is already known, and a non-irradiation moving step for acquiring the position of the sample by irradiating an area including the alignment portion but not including the cross section processing position with an electron beam or the focused ion beam before performing the protective film forming step, and then relatively moving the cross section processing position to an area to be irradiated with the focused ion beam without emitting the electron beam or the focused ion beam on the basis of the known positional relationship is further provided.

In this configuration, the organic substance is prevented from becoming damaged without necessity of irradiation of the organic substance on the surface of the sample with the electron beam or the ion beam for aligning the cross section processing position.

Preferably, the sample is irradiated with the focused ion beam from at least two or more different directions when irradiating the sample with the focused ion beam in the protective film forming step.

In this configuration, since a position to be irradiated with the ion beam is changed, a complex shape of the organic substance on the surface of the sample (for example, depressions or side walls) is also irradiated with the ion beam, so that the protective film is formed sufficiently.

Preferably, different focused ion beam barrels are used for a case where the focused ion beam is emitted in the protective film forming step and for a case where the focused ion beam is emitted in the cross section processing step.

In this configuration, it is not necessary to change the accelerating voltage of one focused ion beam barrel being used for both steps in mid course, so that an advantage such that a stable ion beam can be obtained immediately is achieved.

Also, the ion beam can be emitted at an angle with respect to the surface of the sample in the protective film forming step and emitted vertically with respect to the surface of the sample in the cross section processing step by changing the angles of mounting the respective focused ion beam barrels. If the one focused ion beam barrel is used for the both steps, it is necessary to tilt the sample using a tilt mechanism of the sample stage. However, in this case, it is not necessary to use such the tilt mechanism, so that the operation by the operator is simplified.

Furthermore, the ion used in the ion beam may be differentiated between the protective film forming step and the cross section processing step, so that it is possible to select the ion species which gives less damage to the organic substance on the surface of the sample in the protective film forming step than the ion beam used in the cross section processing step, so that the damage of the organic substance is prevented further effectively.

Preferably, a thin section fabricating step for performing the cross section processing at an opposed position from the cross section processing position by a predetermined thickness and fabricating a thin section including the cross section processing position as the surface thereof is provided. In this configuration, a TEM (transmission electron microscope) sample may be fabricated.

A method of manufacturing a cross section observation sample according to the invention is a method of manufacturing a cross section observation sample by irradiating a sample having a layer or a structure of an organic substance on a surface thereof with a focused ion beam using a focused ion beam apparatus and performing the cross section processing at a cross section processing position thereof comprising: a protective film forming step for irradiating the surface of the sample including the cross section processing position with the focused ion beam under the existence of source gas as a protective film and forming the protective film on the surface of the layer or the structure of the organic substance; and a cross section processing step for performing the cross section processing by irradiating the cross section processing position formed with the protective film with the focused ion beam at a voltage higher than an accelerating voltage in the protective film forming step.

Preferably, a thin section fabricating step for performing the cross section processing at an opposed position from the cross section processing position by a predetermined thickness and fabricating a thin section including the cross section processing position as the surface thereof is provided. In this configuration, a TEM (transmission electron microscope) sample may be fabricated.

According to the invention, the cross section of the sample formed with the organic substance on the surface thereof is acquired with high degree of accuracy.

BRIEF DESCRIPTION OF THE DRAWINGS

FIGS. 4(a)-4(f) are drawings showing processes in a first protective film forming step;

FIGS. 6(g)-6(j) are drawings showing processes in a second protective film forming step and a cross section processing step;

DETAILED DESCRIPTION OF THE PREFERRED EMBODIMENTS

Figure 1:
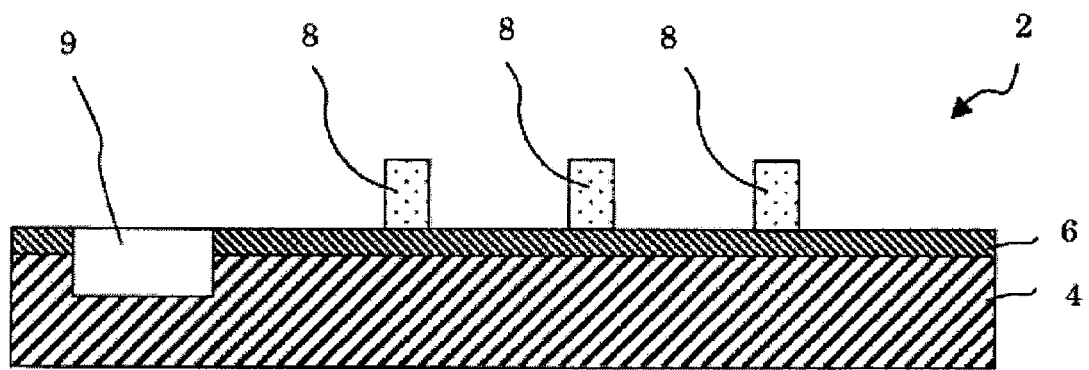
FIG. 1 is a cross-sectional view showing an example of a configuration of a sample.

Referring now to the drawings, embodiments of the invention will be described.

FIG. 1 is a cross-sectional view showing an example of a configuration of a sample 2 which is a object of processing in a cross section processing method according to an embodiment of the invention.

The sample 2 is formed with an anti-reflective layer (BARC: Bottom Anti Reflective Coating) 6 on a surface of a semiconductor device 4, and is formed with a photoresist pattern 8 in an ribbed pattern on the surface of the anti-reflective layer 6. The anti-reflective layer 6 is an organic coating and improves accuracy of the pattern at the time of exposure and development of a photoresist. The photoresist pattern 8 includes a plurality of linear projections arranged in parallel at a distance from each other.

An alignment mark (alignment portion) 9 composed of a hole which penetrates through the anti-reflective layer 6 and partly reaches the semiconductor device 4 is formed on the surface of the semiconductor device 4 outside the photoresist pattern 8.

The anti-reflective layer 6 is also described as a "layer of an organic substance", and the photoresist pattern 8 is also described as a "structure of an organic substance". As other examples of the layer or the structure of the organic substance, there are various organic films and structures such as a Low-k film.

Figure 2:
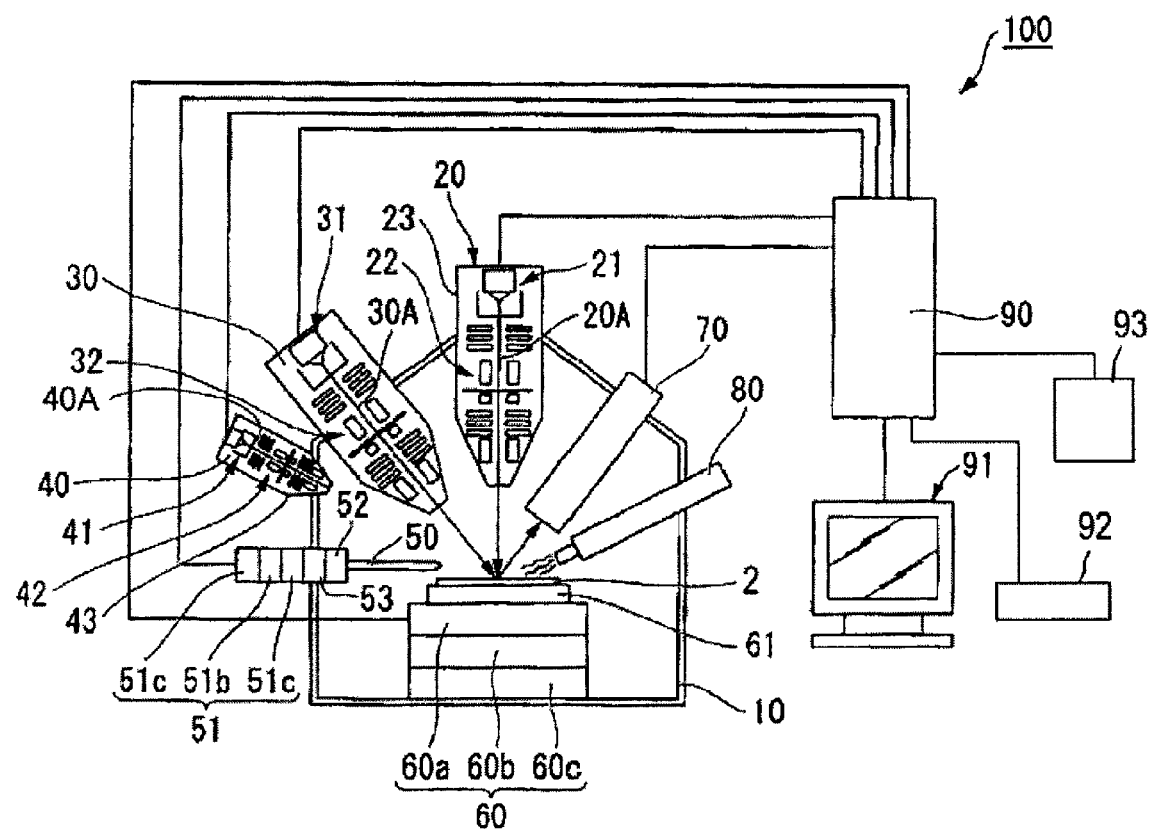
FIG. 2 is a block diagram showing a general configuration of a focused ion beam apparatus.

FIG. 2 is a block diagram showing a general configuration of a focused ion beam apparatus 100 suitably used in the cross section processing method according to the embodiment of the invention. In FIG. 2, the focused ion beam apparatus 100 includes a vacuum chamber 10, an ion beam irradiation system (also described as "focused ion beam barrel") 20, an electron beam irradiation system 30, an argon ion beam irradiation system 40, a nanoforceps 50, a sample stage 60, a secondary charged electron detector 70, a gas gun 80, and a control unit 90. The interior of the vacuum chamber 10 is decompressed to a predetermined degree of vacuum, and part or all of components of the focused ion beam apparatus 100 are arranged in the vacuum chamber 10.

The sample stage 60 movably supports a sample table 61, and the sample 2 is placed on the sample table 61. Then, the sample stage 60 includes a moving mechanism which allows five-axis displacement of the sample table 61. This moving mechanism includes a XYZ moving mechanism 60b configured to move the sample table 61 in parallel to the horizontal plane and along an X-axis and a Y-axis orthogonal to each other, and a Z-axis orthogonal to the X-axis and the Y-axis, a rotation mechanism 60c configured to cause the sample table 61 to rotate about the Z-axis, and a tilt mechanism 60a configured to rotate the sample table 61 about the X-axis (or the Y-axis). The sample stage 60 moves the sample 2 to a position of irradiation of an ion beam 20A by five-axis displacement of the sample table 61.

The control unit 90 includes a CPU as a central processing unit, a storage unit (RAM and ROM) 93 configured to store data, programs, and the like, and a computer having an input port and an output port for inputting and outputting signals with respect to an external equipment. The control unit 90 controls respective components of the focused ion beam apparatus 100 by executing various types of processing by the CPU on the basis of the program stored in the storage unit 93. The control unit 90 is electrically connected to control wirings or the like of the ion beam (hereinafter, the focused ion beam is referred to simply as "ion beam" as needed) irradiation system 20, the electron beam irradiation system 30, the argon ion beam irradiation system 40, the nanoforceps 50, the secondary charged electron detector 70, and the sample stage 60.

The control unit 90 is configured to drive the sample stage 60 on the basis of instructions of software or inputs by an operator, and adjust the position or a posture of the sample 2, thereby adjusting the position of irradiation and an angle of irradiation of the ion beam 20A onto the surface of the sample 2. The control unit 90 is also adapted to drive a forceps stage 51 and a clamping mechanism 53 to adjust the position and the posture of the nanoforceps 50 so as to allow holding of the sample 2 by the nanoforceps 50.

An input unit 92 such as a keyboard or the like for acquiring input instruction from the operator is connected to the control unit 90.

When the sample 2 is irradiated with the electron beam or the ion beam, secondary charged particles are generated, and is detected by the secondary charged electron detector 70. The control unit 90 converts the secondary charged particles detected by the secondary charged electron detector 70 into a brightness signal and generates an image data showing a sample surface, and then generates a sample image on the basis of the image data. The sample image is outputted to a display device (display) 91 connected to the control unit 90.

Then, when the operator specifies a predetermined position on the sample image (the alignment mark 9 described above), the control unit 90 acquires a specified coordinate, and calculates the cross section processing position on the basis of the positional relationship between the cross section processing position of the sample 2 and the alignment mark 9. The control unit 90 moves the sample stage 60 on the basis of the result of calculation so that the cross section processing position of the sample 2 falls within an area to be irradiated with the ion beam. The positional relationship between the cross section processing position and the alignment mark 9 is stored in the storage unit 93 in advance as a known data. In this manner, the cross section processing position can be moved into the area to be irradiated with the ion beam without irradiating the sample 2 with the electron beam or the ion beam.

The ion beam irradiation system (hereinafter, referred to as "second focused ion beam barrel" as needed) 20 includes an ion source 21 configured to generate ion, and an ion optical system 22 configured to form the ion (Ga in this example) flowed out from the ion source 21 into the focused ion beam and causes the same to perform scanning. The sample 2 on the sample stage 60 in the vacuum chamber 10 is irradiated with the ion beam 20A as a charged particle beam from the ion beam irradiation system 20 having an ion beam barrel 23. At this time, the secondary charged particles such as secondary ion or secondary electrons are generated from the sample 2. The secondary charged particles are detected by the secondary charged electron detector 70, so that the image of the sample 2 is acquired. The ion beam irradiation system 20 performs the cross section processing (etching) of the sample 2 within a range of irradiation by increasing an amount of irradiation of the ion beam 20A.

The ion optical system 22 includes, for example, a condenser lens configured to focus the ion beam 20A, an aperture configured to narrow the ion beam 20A, an aligner configured to adjust an optical axis of the ion beam 20A, an objective lens configured to focus the ion beam 20A onto the sample, and a deflector configured to scan the ion beam 20A on the sample.

The electron beam irradiation system 30 includes an electron source 31 configured to emit electrons, and an electron optical system 32 configured to form the emitted electrons from the electron source 31 into a beam-shape and perform scanning. By irradiating the sample 2 with an electron beam 30A emitted from the electron beam irradiation system 30, the secondary electrons are generated from the sample 2, and the generated secondary electrons are detected by the secondary charged electron detector 70 for acquiring an image of the sample 2. Here, the electron beam 30A emitted from irradiation system 30 is emitted on the sample 2 at the same position as the ion beam 20A.

In the invention, a charged particle beam device having no electron beam irradiation system 30 may be employed.

The secondary charged electron detector 70 detects the secondary charged particles (secondary electrons or secondary ion) generated from the sample 2 when the sample 2 is irradiated with the ion beam 20A or the electron beam 30A.

The argon ion beam irradiation system (hereinafter, referred to as "first focused ion beam barrel" as needed) 40 includes an argon ion source 41, an argon ion optical system 42, and an argon ion beam barrel 43.

An argon ion beam 40A is emitted from the argon ion beam irradiation system 40, and by supplying compound gas from the gas gun 80, a protective film may be formed on the surface of the sample 2.

An irradiation axis of the ion beam irradiation system 20 is vertical to the surface of the sample table 61, so that the FIB for fabricating the sample cross section can be emitted vertically with respect to the sample. An irradiation axis of the electron beam irradiation system 30 forms a predetermined angle with respect to the irradiation axis of the ion beam irradiation system 20, so that the electron beam can be emitted obliquely with respect to the cross section formed by the cross section processing with the FIB from the ion beam irradiation system 20. In the same manner, the irradiation axis of the argon ion beam irradiation system 40 forms a predetermined angle with respect to the irradiation axis of the ion beam irradiation system 20, so that the electron beam can be emitted obliquely with respect to the sample 2.

The respective irradiation systems 20, 30, 40 are arranged so that the three beams emitted therefrom intersects at the same area (the same position on the sample).

The gas gun 80 emits predetermined gas such as deposition gas or etching gas to the sample 2. By irradiating the sample 2 with the ion beam 20A or the argon ion beam 40A while supplying compound gas as the protective film from the gas gun 80, local precipitation (deposition) of the gas component is achieved in the vicinity of an area to be irradiated with the ion beam 20A and the argon ion beam 40A so that the protective film is formed. By irradiating the sample 2 with the ion beam 20A while supplying the etching gas from the gas gun 80, the speed of etching of the sample by the ion beam 20A may be increased.

Subsequently, the cross section processing method according to the embodiment of the invention will be described.

Figure 3:
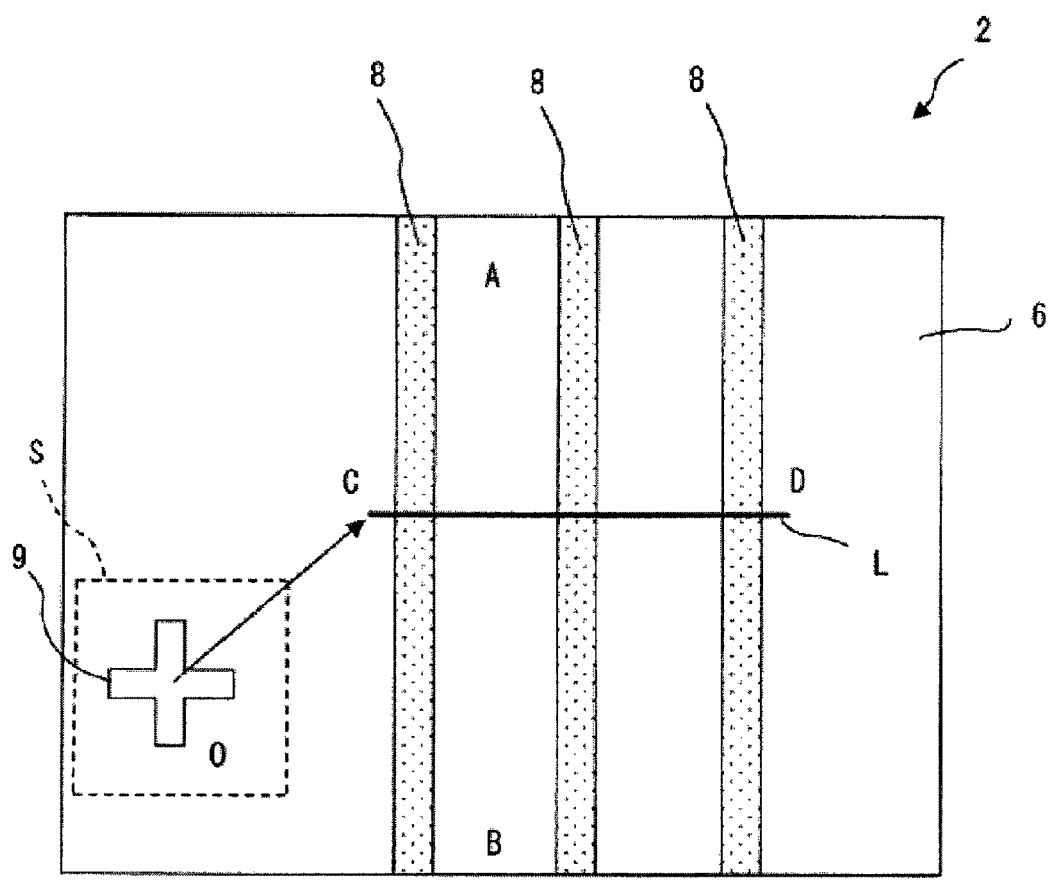
FIG. 3 is a drawing showing a non-irradiation moving step for determining a cross section processing position for performing cross section processing.

FIG. 3 shows a non-irradiation moving step for determining a cross section processing position L on the surface of the sample 2 where the cross section processing with respect to the sample 2 is performed with the FIB. The cross section processing position L extends linearly on the surface of the sample 2 and, when determining defect or the like of the sample 2, the cross section after the processing is observed.

First of all, when an area S on the surface of the sample 2 including an alignment portion but not including the cross section processing position L is irradiated with the electron beam or the ion beam, a surface image of the sample 2 is acquired. When the operator specifies (a center O of) the alignment mark 9 on the display device 91, the control unit 90 acquires the specified coordinate, and reads out a known positional relationship between the cross section processing position L and the alignment mark 9 from the storage unit 93. Then, the control unit 90 calculates the coordinate of the cross section processing position L on the basis of this positional relationship and writes the same in the storage unit 93. Then, the control unit 90 moves the sample stage 60 on the basis of the result of calculation so that the cross section processing position L is positioned within the area to be irradiated with the ion beam (or the electron beam) when emitting the ion beam (or the electron beam) in the subsequent step.

In this manner, since the cross section processing position L can be moved to fall within the area to be irradiated with the ion beam without irradiating the sample 2 with the electron beam or the ion beam, it is not necessary to irradiate the organic substance on the surface of the sample 2 with the electron beam or the ion beam for the alignment of the cross section processing position L, so that the organic substance is prevented from becoming damaged.

Subsequently, a protective film forming step for forming the protective film by irradiating the surface of the sample 2 with the ion beam will be described.

As the method of forming the protective film in the invention includes a) a method of forming the protective film at once under one beam irradiation condition (accelerating voltage) and b) a method of laminating a plurality of the protective films under a plurality of beam irradiation conditions (accelerating voltage). Also, there are c) a method of forming the protective film using the focused ion beam barrel which is used in a cross section processing step, and d) a method of forming the protective film using a focused ion beam barrel different from the focused ion beam barrel which is used in the cross section processing step. Therefore, there are four methods of a) to d) altogether. In any of these methods, the focused ion beam is emitted at a voltage lower than the accelerating voltage in the cross section processing step to form the protective film.

Among these methods, a method in which the method b) and the method d) are combined as the most preferable method will be described as an embodiment of the invention.

In other words, the protective film forming step in this embodiment includes two steps of i) irradiating the surface of the sample 2 with the focused ion beam at a first accelerating voltage, and then ii) irradiating the surface of the sample 2 with the focused ion beam at a second accelerating voltage higher than the first accelerating voltage. Then, in the cross section processing step, which is a post-process, the cross section processing is performed by iii) irradiating the surface of the sample with the focused ion beam at a voltage higher than the accelerating voltage in the protective film forming step.

The step i) (hereinafter, referred to as a "first protective film forming step" as needed) will be described with reference to FIG. 4. First of all, the cross section processing position L is placed in the area to be irradiated with the ion beam without emitting the ion beam (or the electron beam) as shown in FIG. 3, the surface of the sample 2 including the cross section processing position L is irradiated with the ion beam 40A from the first focused ion beam barrel 40 while supplying compound gas as the protective film from the gas gun 80 (FIG. 4(a)). At this time, by setting an accelerating voltage V1 for emitting the ion beam 40A to a value on the order of 1 kV at maximum, more preferably, to a value on the order of 500 V at maximum, damage of the organic substance by the ion beam on the surface of the sample 2 is reduced, and the protective film (first protective film) can be formed while preventing the organic substance from becoming damaged.

As the protective film, Pt, W, and C may be exemplified. In a practical sense, however, the compound gas which forms the protective film is an organic compound including Pt, the protective film is an organic film including Pt, W, and C.

In this embodiment, the ion beam 40A is emitted at a predetermined angle θ (but smaller than 90°, 45° in this example) with respect to the surface of the sample 2. In this configuration, the depressions or side walls of the complex shape of the organic substance on the surface of the sample 2 (the photoresist pattern 8 having projections and depression as shown in FIG. 1, for example) may be irradiated with the ion beam 40A, so that the protective film can be formed sufficiently.

In this embodiment, the predetermined area including the cross section processing position L is irradiated with the ion beam 40A from two or more different directions (FIGS. 4(b) to 4(f)). In this configuration, since a direction of emission of the ion beam 40A is changed, the depressions or the side walls of the complex shape of the organic substance on the surface of the sample 2 (the photoresist pattern 8 having projections and depression as shown in FIG. 1, for example) may be irradiated with the ion beam 40A, so that the protective film can be formed sufficiently.

Emitting the ion beam 40A from the different directions will be described in conjunction with FIGS. 4(a) to 4(f). FIGS. 4(a) to 4(f) are views of the position of the sample 2 when the direction of emission of the ion beam 40A is kept constant viewed from above, and the position of the sample 2 can be set to those shown in any one of FIGS. 4(a) to 4(f) by rotating the sample stage 60 on a plane.

First of all, the ion beam 40A is emitted along the direction A-B in which the projections of the photoresist pattern 8 extend (FIG. 4(a)). Here, the expression "the ion beam 40A is emitted along the direction A-B" means that an angle formed between the direction of emission of the ion beam 40A (irradiation axis) and a segment AB is equal to the angle θ between the surface of the sample 2 and the direction of emission of the ion beam 40A.

Figure 5A:
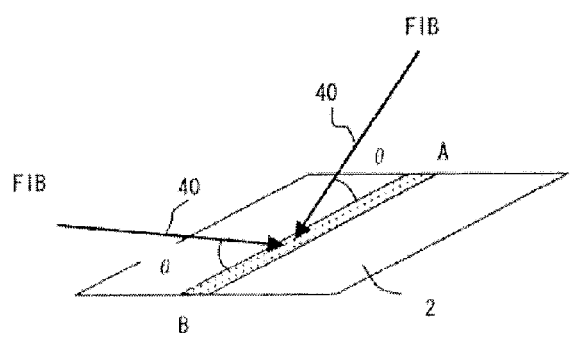
FIGS. 5(a) and 5(b) are drawings showing directions of irradiation of the sample with an ion beam.

Subsequently, when the sample stage 60 is rotated on the plane by 180° and the surface of the sample 2 is irradiated with the ion beam 40A (FIG. 4(b)), the ion beam 40A is emitted from a direction in symmetry with the direction of emission shown in FIG. 4(a) with respect to a plane extending along the direction A-B and vertical to the segment AB (FIG. 5(a)). In this configuration, since the sample is irradiated with the ion beam from two different directions (corresponding to FIGS. 4(a) and 4(b)), the respective portions of the organic substance having a complex shape on the surface of the sample 2 (the photoresist pattern 8 having projections and depression as shown in FIG. 1, for example) may be irradiated with the ion beam 40A, so that the protective film can be formed sufficiently also on the depressions or the side walls which are hidden by the projections.

The sample stage 60 is rotated further by 180° on the plane, and the surface of the sample 2 is irradiated with the ion beam 40A again from the same direction as in FIG. 4(a) (FIG. 4(c)). In the same manner, the sample stage 60 is rotated further by 180° on the plane from the state shown in FIG. 4(c), and the surface of the sample 2 is irradiated with the ion beam 40A again from the same direction as in FIG. 4(b) (FIG. 4(d)).

Figure 5B:
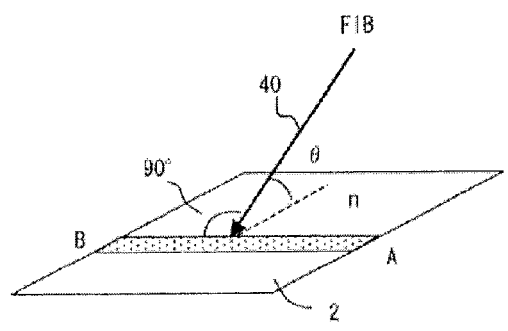

Furthermore, the sample stage 60 is rotated further by 90° leftward on the plane from the state shown in FIG. 4(d), and the surface of the sample 2 is irradiated with the ion beam 40A from the direction vertical to the direction in FIG. 4(a) (FIG. 4(e)). In this case, as shown in FIG. 5(b), the angle formed between the direction of emission of the ion beam 40A (irradiation axis) and the segment AB is 90°. In contrast, the angle formed between a normal line n of the segment AB and the direction of emission of the ion beam 40A is equal to the angle θ formed between the surface of the sample 2 and the direction of emission of the ion beam 40A. In this manner, since the sample is irradiated with the ion beam 40A also from the direction vertical to the direction shown in FIG. 4(a), the respective portions of the organic substance having a complex shape on the surface of the sample 2 (the photoresist pattern 8 having projections and depression as shown in FIG. 1, for example) may further be irradiated with the ion beam 40A, so that the protective film can be formed sufficiently also on the depressions or the side walls which are hidden by the projections.

Subsequently, the sample stage 60 is rotated further by 180° on the plane from the state shown in FIG. 4(e), and the surface of the sample 2 is irradiated with the ion beam 40A (FIG. 4(f)). In the case of FIG. 4(f), the ion beam 40A is emitted from the direction in symmetry with the direction of emission shown in FIG. 4(e) with respect to the surface passing through the segment AB.

In this embodiment, emission of the ion beam 40A along the direction A-B in which the projections of the photoresist pattern 8 extend four times (FIGS. 4(a) to 4(d)), while the number of times of emission of the ion beam 40A from the direction vertical to the direction A-B is small (two times of FIGS. 4(e) and 4(f)). It is because emitting the ion beam 40A along the direction A-B allows the depressions of the photoresist pattern 8 to be irradiated with the ion beam 40A and hence it is easier to form the protective film thereon. The same effect is achieved by changing the duration of irradiation instead of controlling the number of times of irradiation.

Subsequently, the step ii) (hereinafter, referred to as a "second protective film forming step" as needed) and the step iii) (cross section processing step) will be described with reference to FIGS. 6(g) to 6(j). In the second protective film forming step, the protective film (second protective film) is formed by irradiating the surface of the sample 2 including the cross section processing position L with the ion beam 20A from the second focused ion beam barrel 20 while supplying the compound gas which forms the protective film from the gas gun 80 (FIG. 6(h)). At this time, by setting an accelerating voltage V2 for emitting the ion beam 20A to a value higher than the accelerating voltage V1, the second protective film can be formed efficiently on the first protective film. In other words, since the organic substance on the surface of the sample 2 is protected by the first protective film, the ion beam can be emitted at a relatively high accelerating voltage without considering the damage of the organic substance by the ion beam.

The accelerating voltage V2 may be, for example, on the order of 5 to 40 kV and, more preferably, on the order of 15 to 30 kV. The second protective film may have a similar composition as the first protective film, and having the same composition as the first protective film is preferable in terms of production efficiency.

Since the second focused ion beam barrel 20 is used also in the cross section processing step as the post-process, the ion beam 20A is emitted vertically with respect to the surface of the sample 2.

In this embodiment, a third protective film forming step for forming the protective film (a third protective film) with the electron beam is included between the first protective film forming step and the second protective film forming step (FIG. 6(g)). The third protective film forming step is a step for forming the protective film by irradiating the surface of the sample 2 including the cross section processing position L with the electron beam 30A from the electron beam irradiation system 30 while supplying the compound gas as the protective film from the gas gun 80.

Although the third protective film forming step is not essential, since the electron beam cause less interfusion of impurities into the protective film in comparison with the formation of the protective film with the ion beam, and hence there is no injection of beam species into the sample, the sample is not damaged. Also, by forming the protective film in the third protective film forming step, injection of the beam species which might be generated in the second protective film forming step may be restrained.

In the cross section processing step following after the second protective film forming step, the ion beam 20A is emitted at an accelerating voltage V3 which is higher than the accelerating voltage V1 in the first protective film forming step, thereby performing the cross section processing (FIG. 6(i)). The ion beam 20A is emitted from the second focused ion beam barrel 20 vertically with respect to the surface of the sample 2. In the cross section processing, the ion beam 20A is narrowed and scanning along the cross section processing position L is performed therewith. Furthermore, an area R of the sample 2 positioned on the nearer side than the cross section processing position L is ground deeply, so that the cross section is exposed at the cross section processing position L.

The accelerating voltage V3 must simply be equal to or larger than the accelerating voltage V2 in the second protective film forming step and may be the same as the accelerating voltage V2. By setting the accelerating voltage V2 and the accelerating voltage V3 equal to each other, it is not necessary to change the accelerating voltage.

Furthermore in this embodiment, the focused ion beam barrel 40 which emits the ion beam 40A in the first protective film forming step is different from the focused ion beam barrel 20 configured to emit the ion beam 20A in the cross section processing step.

In this configuration, when the accelerating voltage V1 of the ion beam 40A in the first protective film forming step is lower than the accelerating voltage V3 of the ion beam 20A in the cross section processing step, it is not necessary to change the accelerating voltage of one focused ion beam barrel being used for both steps in mid course, so that an advantage such that a stable ion beam can be obtained immediately is achieved.

Since the ion beam 40A is emitted at the angle θ with respect to the surface of the sample 2 in the first protective film forming step and, in contrast, the ion beam 20A is emitted vertically with respect to the surface of the sample 2 in the cross section processing step, it is necessary to tilt the sample 2 using a tilt mechanism of the sample stage 60 in a case where the one focused ion beam barrel is used in the both steps. In contrast, since the first focused ion beam barrel 40 and the second focused ion beam barrel 20 which are different in mounting angle with respect to the sample 2 are used respectively in the both steps, it is not necessary to use the tilt mechanism of the sample stage 60, so that the operation of the operator is simplified.

Furthermore, ion used in the ion beam for the first protective film forming step is different from ion used in the ion beam for the cross section processing step, and if the one focused ion beam barrel is used for the both steps, the ion cannot be changed. In other words, since an inactive argon ion beam is used in the first protective film forming step, damage of the organic substance on the surface of the sample 2 due to the injection of the ion species by the ion beam can be reduced in comparison with a Ga ion beam used in the cross section processing step, so that the damage of the organic substance is prevented further effectively.

As the ion species of the ion beam sued in the first protective film forming step, helium, neon, and krypton may be exemplified in addition to argon, and these ion species causes less damage to the organic substance in comparison with other types of ion (Ga, for example).

In the invention, in the case where "the accelerating voltage in the cross section processing step is higher than the accelerating voltage in the protective film forming step", if there are a plurality of protective film forming steps, what is essential is that the accelerating voltage in the cross section processing step is higher than the accelerating voltage of one of these steps (first protective film forming step).

Also, in the invention, in the case where "the different focused ion beam barrels are used for the case where the ion beam is emitted in the protective film forming step and for the case where the ion beam is emitted in the cross section processing step", if there are a plurality of the protective film forming steps, what is essential is that the focused ion beam barrel used in one of the steps (the first protective film forming step) is different from the focused ion beam barrel used in the cross section processing step.

A thin section fabricating step may be performed following to the cross section processing step (FIG. 6(j)). In the thin section fabricating step, the focused ion beam 20A is emitted at the accelerating voltage V3 to an opposed position L2 located at a predetermined thickness from the cross section processing position L to perform the cross section processing to fabricate a thin section 200 having the cross section processing position L and the opposed position L2 as opposed surfaces. At this time, an area R2 of the sample 2 positioned on the nearer side than the opposed position L2 is ground deeply, at the accelerating voltage V3 so that the cross section is exposed at the opposed position L2.

In this manner, a TEM sample in which the thin section 200 is raised from the areas R, R2 of the sample 2 may be fabricated. Then, the thin section 200 is taken out using the nanoforceps 50 and held on a predetermined sample table, so that the TEM observation can be performed.

Figure 7:
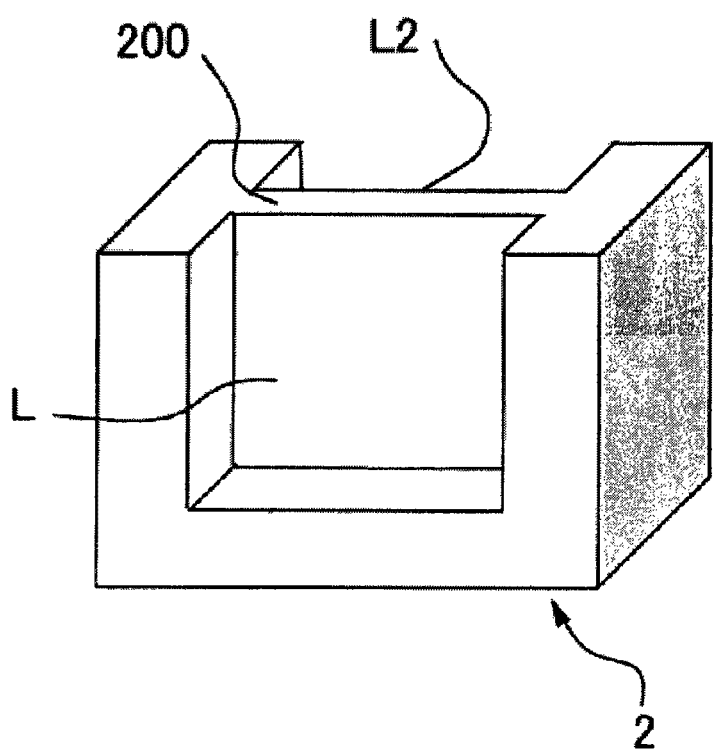
FIG. 7 is a drawing showing a configuration of the sample formed with a thin section.

FIG. 7 shows a configuration of the sample 2 in which the thin section 200 is formed. The cross section processing position L and the opposed position L2 are exposed by the cross section processing to form the thin section 200.

Figure 8:
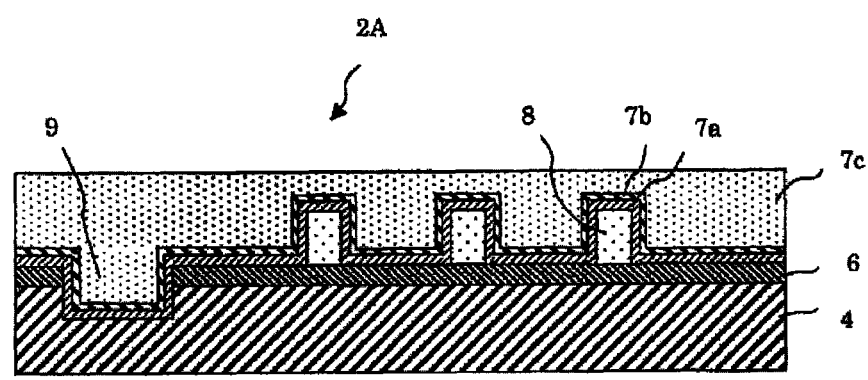
FIG. 8 is a diagrammatic cross-sectional view showing a configuration of a cross section observation sample according to an embodiment.

FIG. 8 shows a diagrammatic cross-sectional view showing a configuration of a cross section observation sample fabricated by the cross section processing method according to the embodiment of the invention.

A cross section observation sample 2A includes the anti-reflective layer 6 formed on the surface of the semiconductor device 4 and the photoresist pattern 8 formed on the surface of the anti-reflective layer 6. The surface of the photoresist pattern 8 is formed with a first protective film 7a, a third protective film 7b, and a second protective film 7c formed in this order. The second protective film 7c is thicker than the first protective film 7a and the third protective film 7b.

Figure 9:
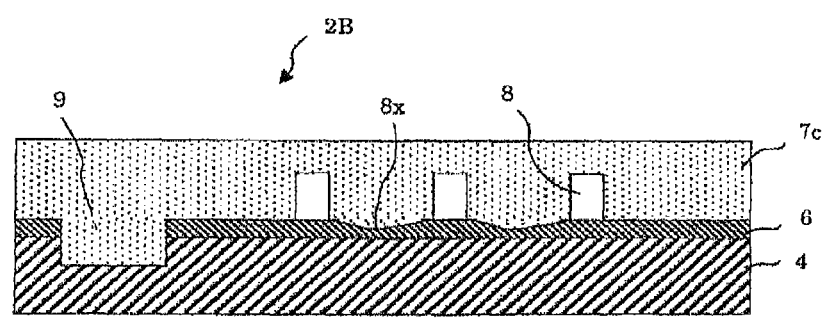
FIG. 9 is a diagrammatic cross-sectional view showing a configuration of the cross-section observation sample in the related art.

In contrast, FIG. 9 shows a diagrammatic cross-sectional view showing a configuration of a cross section observation sample 2B fabricated by the cross section processing method in the related art in which the accelerating voltages in the protective film forming step and the cross section processing step are the same (30 kV). In the cross section processing method in the related art, the argon ion beam is emitted using the focused ion beam barrel which is the same as that used in the cross section processing step in the protective film forming step to form the protective films at once.

It is understood from FIG. 9 that since the accelerating voltage of the ion beam in the protective film forming step is high, the anti-reflective layer 6 as the organic film is ground between the depressions of the photoresist pattern 8 and hence a deformed portion 8x is formed, whereby the accurate cross section cannot be obtained.

The invention is not limited to the embodiment shown above and, needless to say, the invention covers various modifications and equivalents included in the spirit and scope of the invention.

It is therefore intended that the foregoing detailed description be regarded as illustrative rather than limiting, and that it be understood that it is the following claims, including all equivalents, that are intended to define the spirit and scope of this invention.

What is claimed is:

1. A cross section processing method to be performed on a sample having a patterned surface feature comprising an organic substance on a surface by irradiating the sample at a cross section processing position thereof with a first and a second focused ion beam using a focused ion beam apparatus, the method comprising:

forming a protective film on the surface of the patterned surface feature by irradiating the surface of the sample with the first focused ion beam at a first accelerating voltage under the presence of a source gas to form the protective film, wherein the first accelerating voltage has a maximum of value of 1 kV and does not deform the patterned surface feature; and irradiating the cross section processing position with the second focused ion beam at a second accelerating voltage higher than the first accelerating voltage, wherein ions of the second focused ion beam are different from ions of the first focused ion beam.

2. The cross section processing method according to claim 1, wherein the sample further includes an alignment portion whose positional relationship with the cross section processing position is already known, and before forming a protective film on the patterned surface feature, irradiating an area including the alignment portion but not including the cross section processing position with an electron beam or the second focused ion beam before forming the protective film, and then relatively moving the cross section processing position to an area to be irradiated with the second focused ion beam without emitting the electron beam or the focused ion beam on the basis of the known positional relationship.

3. The cross section processing method according to claim 1, wherein the sample is irradiated with the first focused ion beam from at least two or more different directions arranged by rotating the sample on a plane when irradiating the sample to form the protective film.

4. The cross section processing method according to claim 1, wherein the ions of the first focused ion beam, comprise ions including argon, helium, krypton, or neon, and the ions of the second focused ion beam comprise gallium ions.

5. The cross section processing method according to claim 1 comprising forming a thin section of the sample by processing at a position opposite from the cross section processing position and fabricating the thin section including the cross section processing position as a continuous parallel surface thereof.

6. The cross section processing method according to claim 1, further comprising forming a second protective film on the sample by irradiating the patterned surface feature with the second focused ion beam at the second accelerating voltage.

7. A cross section processing method to be performed on a sample having a patterned surface feature comprising an organic substance on a surface by irradiating the sample at a cross section processing position thereof with a first and a second focused ion beam using a focused ion beam apparatus, the method comprising:
  irradiating the patterned surface feature with the first focused ion beam at a first accelerating voltage and then irradiating the patterned surface feature with the second focused ion beam at a second accelerating voltage which is higher than the first accelerating voltage under the presence of a source gas to form a protective film, wherein the first accelerating voltage has a maximum of value of 1 kV and does not deform the patterned surface feature; and
  irradiating the cross section processing position with the second focused ion beam at a third accelerating voltage which is higher than the first accelerating voltage, wherein ions of the second focused ion beam are different from ions of the first focused ion beam.

8. The cross section processing method according to claim 7, wherein irradiating the patterned surface feature with the first focused ion beam at the first accelerating voltage forms the protective film, and wherein irradiating the patterned surface feature with the second focused ion beam at a second accelerating voltage forms a second protective film on the first protective film.

9. The cross section processing method according to claim 7, wherein irradiating the cross section processing position with the second focused ion beam at the third accelerating voltage further comprises forming a thin section of the sample by processing at a position opposite from the cross section processing position and fabricating the thin section including the cross section processing position as a continuous surface thereof.

10. A method of manufacturing a cross section observation sample having a patterned surface feature comprising an organic substance on a surface thereof by irradiating the sample with a first and a second focused ion beam using a focused ion beam apparatus and performing the cross section processing at a cross section processing position thereof, the method comprising:
  irradiating the patterned surface feature with the first focused ion beam at a first accelerating voltage having a maximum of value of 1 kV and under the presence of a source gas and forming a protective film on the surface of the patterned surface feature; and
  irradiating the cross section processing position with the second focused ion beam at a second accelerating voltage higher than the first accelerating voltage, wherein ions of the second focused ion beam are different from ions of the first focused ion beam.

11. The method of manufacturing the cross section observation sample according to claim 10 further comprising forming a thin section of the sample by processing at a position opposite from the cross section processing position and fabricating the thin section including the cross section processing position as a continuous parallel surface thereof.

* * * * *